United States Patent [19]
Mookherjee et al.
[11] Patent Number: 4,596,671
[45] Date of Patent: Jun. 24, 1986

[54] USE OF 4(2'-BUTYL) PHENYL ACETATE IN AUGMENTING OR ENHANCING THE LEATHER AROMA OF PERFUME COMPOSITIONS, COLOGNES, PERFUMED POLYMERS AND PERFUMED ARTICLES

[75] Inventors: Braja D. Mookherjee, Holmdel; Robert W. Trenkle, Bricktown, both of N.J.

[73] Assignee: International Flavors & Fragrances Inc., New York, N.Y.

[21] Appl. No.: 656,659

[22] Filed: Oct. 1, 1984

[51] Int. Cl.[4] .......................... A61K 7/46; C11D 3/50
[52] U.S. Cl. .................................. 252/522 R; 560/55; 560/61; 560/64
[58] Field of Search ........................ 252/522 R, 522 A; 560/61, 55, 64

[56] References Cited

U.S. PATENT DOCUMENTS

| | | | |
|---|---|---|---|
| 4,179,571 | 12/1979 | Brody | 560/64 |
| 4,424,394 | 1/1984 | Schneider et al. | 560/61 |
| 4,465,730 | 8/1984 | Okada | 428/246 |

OTHER PUBLICATIONS

Overberger "Chemical Abstracts" vol. 63 (1965) 7113d.

*Primary Examiner*—Werren B. Lone
*Attorney, Agent, or Firm*—Arthur L. Liberman

[57] ABSTRACT

Described is the use for augmenting or enhancing the leather aroma of perfume compositions, colognes, perfumed polymers and perfumed articles including solid or liquid anionic, cationic, nonionic or zwitterionic detergents, fabric softener compositions, fabric softener articles and hair preparations of 4(2'-butyl) phenyl acetate having the structure:

8 Claims, 2 Drawing Figures

USE OF 4(2′-BUTYL) PHENYL ACETATE IN AUGMENTING OR ENHANCING THE LEATHER AROMA OF PERFUME COMPOSITIONS, COLOGNES, PERFUMED POLYMERS AND PERFUMED ARTICLES

BACKGROUND OF THE INVENTION

The present invention provides 4(2′-butyl) phenyl acetate having the structure:

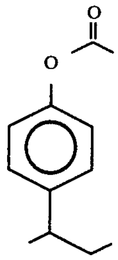

and uses thereof in augmenting or enhancing the aroma of consumable materials including perfume compositions, colognes, perfumed articles and perfumed polymers.

In the perfumery art, there is a considerable need for leathery and ylang oil-like aroma profiles with sweet, floral topnotes. Specifically described herein, is a material having such an organoleptic profile but which does not discolor with age. Such a material has a wide utilization in the presence of perfumery compounds.

Arctander, "Perfume and Flavor Chemicals (Aroma Chemicals)" Volume I, at monograph 1328, discloses ortho-ethyl phenol having the structure:

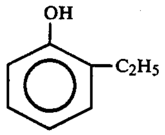

as useful in perfumery, particularly suggesting that orthoethyl phenol could find some use in the "temporarily modern leather" like fragrance types . . . and in various basis requiring . . . leather-like notes. Arctander, however, discloses that orthoethyl phenol carries with it ". . . disadvantages of a phenol: Tendency to discolor in daylight . . . "

Nothing in the prior art, however, infers the utilization of the compound having the structure:

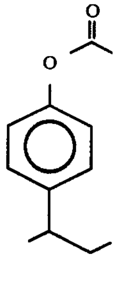

for augmenting or enhancing the leather aroma of perfume compositions, perfumed articles, colognes or perfumed polymers.

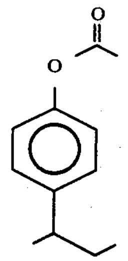

Figure 1:
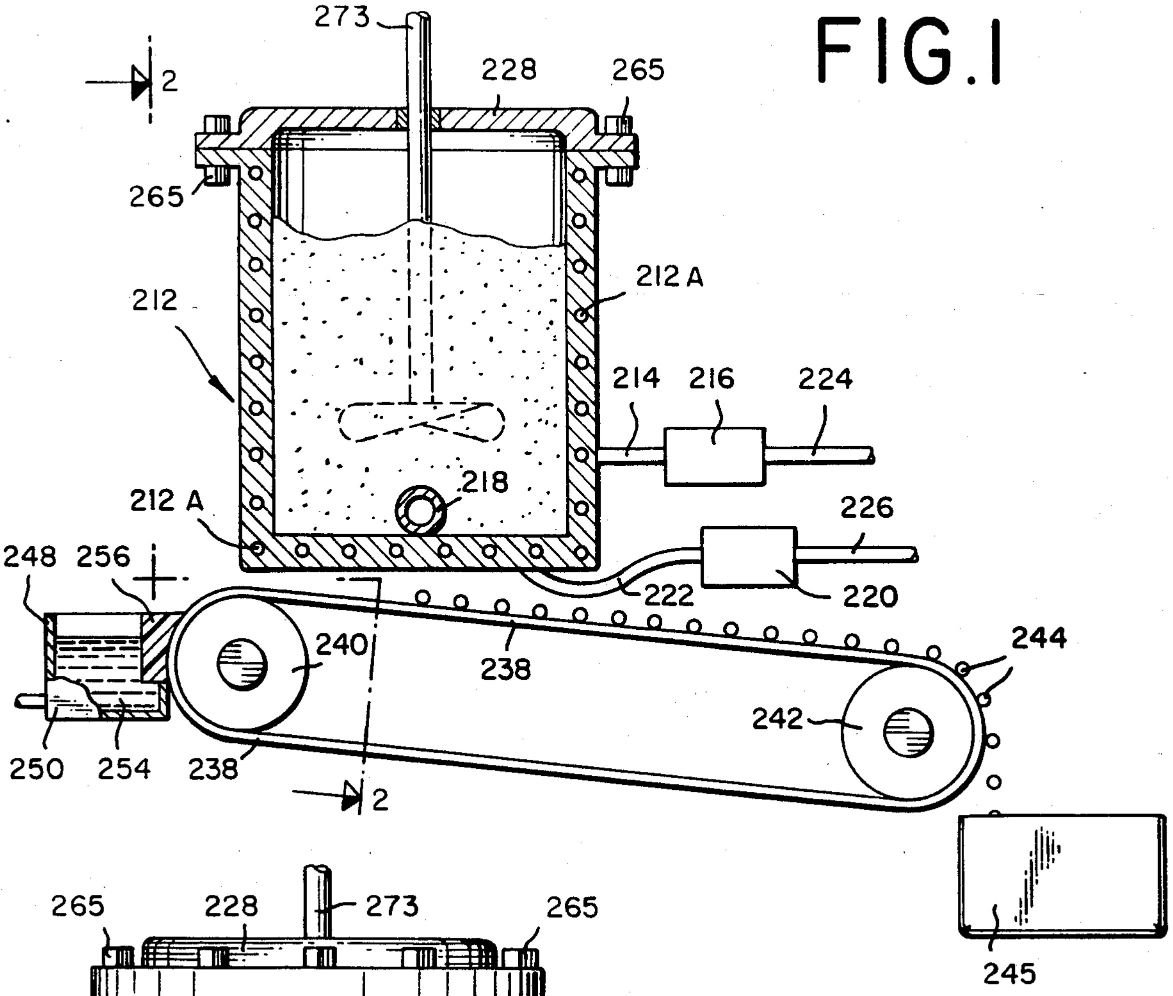
FIG. 1 is a partial side elevation and partial sectional view of an aparatus for forming leather scented polymers using the 4(2′-butyl) phenyl acetate of our invention defined according to the structure.
Figure 2:
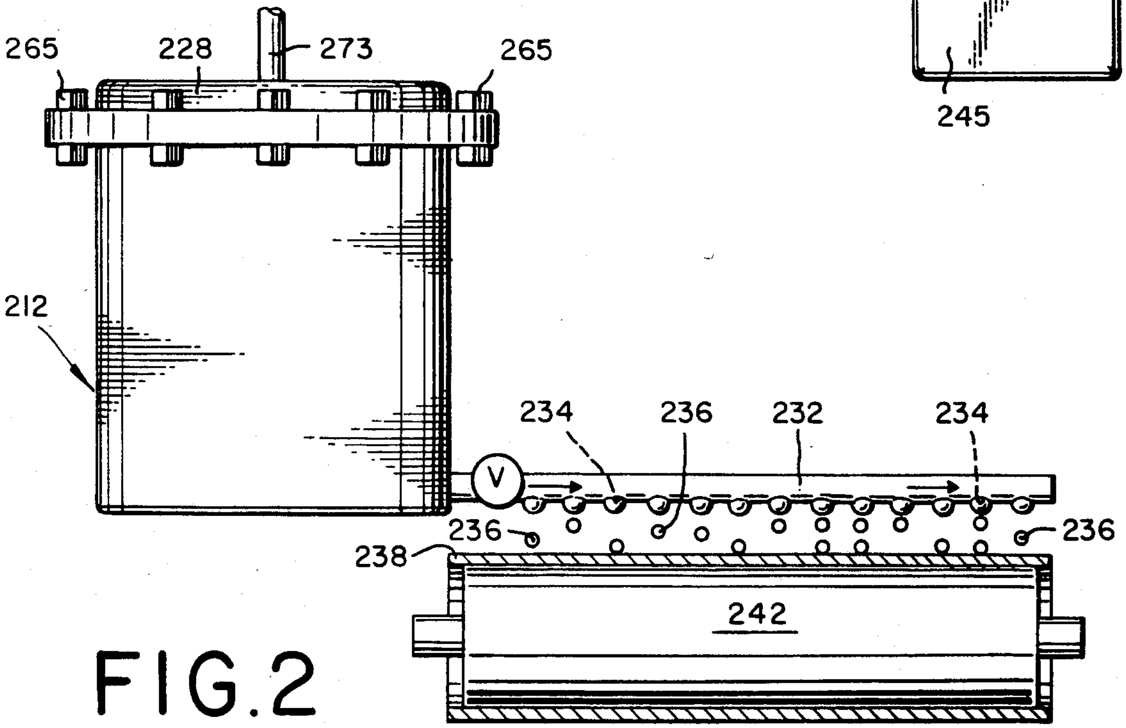

FIG. 2 is a section taken on line 2—2 of FIG. 1.

DETAILED DESCRIPTION OF THE DRAWINGS

Referring to the drawings in FIGS. 1 and 2 in particular, the invention embodied therein comprises a device for forming leather scented polymer pellets (e.g., polyethylene, polypropylene or mixtures of polyepsilon caprolactone and polyethylene or polypropylene or copolymers of polyvinyl acetate and polyethylene or the like) which comprises a vat or container 210 into which a mixture of polymers such as polyethylene and the 4(2′-butyl) phenyl acetate having the structure:

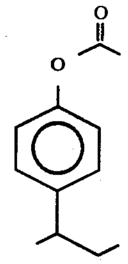

or a mixture of perfume materials including as a key ingredient the 4(2′-butyl) phenyl acetate having the structure:

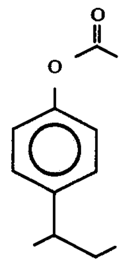

is placed.

The container is closed by an air-tight lid 228 clamped to the container by clamps 265. A stirrer 273 traverses the lid or cover 228 in air-tight manner and is rotated in a suitable manner. A surrounding cylinder 212 having heating coils which are supplied with electrical current through cable 214 from a rheostat or control 216 is operated to maintain the temperature inside the container 210 such that the polymer such as polyethylene in the container will be maintained in a molten or liquid state. It has been found advantageous to employ colorless, odorless polymer such as low density polyethylene with a viscosity ranging between 180 and 220 centistokes and having a melting point in the neighborhood of 220° F. The heater 212 is operated to maintain the upper portion of the container 210 within the temperature range of from 250°-350° F. An additional bottom heater 218 is regulated through a control 220 connected thereto through a connecting wire 222 to maintain the lower portion of the container 210 within a temperature range of from 250° to 350° F.

In accordance with this aspect of the invention, a polymer such as polyethylene or polypropylene is added to the container 210 and is then heated from 10 to 12 hours whereafter a scent or aroma imparting material containing the 4(2'-butyl) phenyl acetate of our invention having the structure:

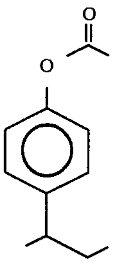

is quickly added to the melt. The material must be compatible with the polymer and forms a homogeneous liquid melt therewith.

The heat resisting mixture containing the 4(2'-butyl) phenyl acetate of our invention having the structure:

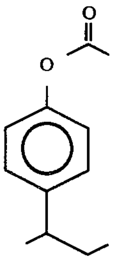

or mixture containing such compound is added to the polymer.

After the 4(2'-butyl) phenyl acetate of our invention having the structure:

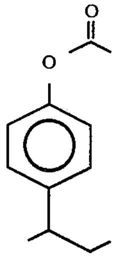

is added to container 210, the mixture is stirred for a few minutes, for example 5-15 minutes, and maintained within the temperature range as previously by the heating coils 212 and 218 respectively. The controls 216 and 220 are connected through cables 224 and 226 to a suitable supply of electric current for supplying the power for heating purposes.

Thereafter the valve "V" is opened permitting the mass to flow outwardly through a conduit 232 having a multiplicity of orifices 234 adjacent the lower side thereof. The outer end of the conduit 232 is closed so that the liquid polymer and substance containing the 4(2'-butyl) phenyl acetate of our invention having the structure:

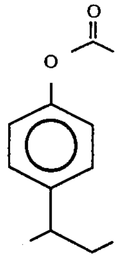

will continuously drop through the orifice 234 downwardly from the conduit 232. During this time the temperature of the polymer and the 4(2'-butyl) phenyl acetate having the structure:

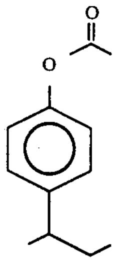

in the container 210 is accurately controlled so that a temperature in the range of from 210° up to 275° F. will be maintained in the material exiting in the conduit 232. The regulation of the temperature through the control 216 and the control 220 is essential in order to insure temperature balance to provide for the continuous dropping or dripping of the molten polymer and the 4(2'-butyl) phenyl acetate having the structure:

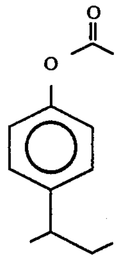

or mixture containing same through the orifices 234 at a range which will insure the formation of droplets 236 which will fall downwardly onto a moving conveyor belt 238 trained to run between conveyor wheels 240 and 242 beneath the conduit 232. When droplets 236 fall onto the conveyor belt 238 they form pellets 244 which harden almost instantaneously and fall off the end of the conveyor 238 into a container 246 which is advantageously filled with water or some other suitable liquid to insure the rapid cooling of each of the pellets. The pellets 244 are then collected from the container 246 and packaged for shipment.

A feature of the invention is the provision for moistening the conveyor belt 238 to insure the rapid formation of the solid polymer leather scented pellets 244 without sticking to the belt. The belt 238 is advantageously of a material which will not normally stick to a melted polymer but the moistening means 248 insures a sufficiently cold temperature of the belt surface for the adequate formation of the pellets 244. The moistening means comprises container 250 which is continuously fed with water 252 to maintain a level 254 for moistening a sponge element 256 which bears against the exterior surface of the belt 238.

The pellets may be formed into sheets which are usable in the leather-like textile materials of U.S. Pat. No. 4,465,730, the specification for which is incorporated by reference herein.

THE INVENTION

It has now been determined that the 4(2'-butyl) phenyl acetate having the structure:

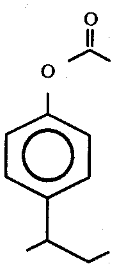

is capable of imparting, augmenting or enhancing a variety of aromas in or to consumable materials.

Briefly, our invention contemplates augmenting, enhancing or imparting fragrances of (or to) such consumable materials as perfumes, perfumed articles (e.g., solid or liquid anionic, cationic, nonionic or zwitterionic detergents, cosmetic powders, fabric softener compositions, dryer-added fabric softener articles and perfumed polymers) and colognes by adding thereto a small but effective amount of the 4(2'-butyl) phenyl acetate having the structure:

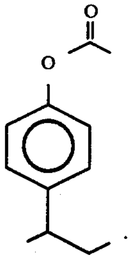

The 4(2'-butyl) phenyl acetate having the structure:

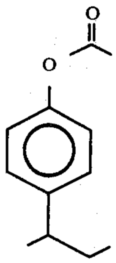

may be prepared from the corresponding phenol having the structure:

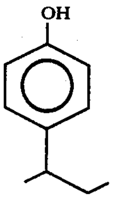

by acetylation under standard esterification conditions using acetic anhydride according to the reaction:

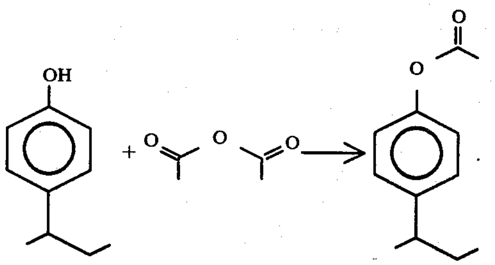

The reaction preferably takes place at reflux conditions in the presence of an inert solvent such as toluene. At the end of the reaction the reaction mass is neutralized and the reaction product is distilled at a temperature in the range of 75°–79° C. and 0.8–2 psi (absolute).

The 4(2'-butyl) phenyl acetate having the structure:

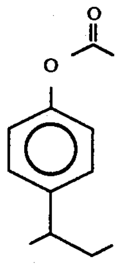

and one or more auxiliary perfume ingredients including, for example, alcohols, aldehydes, ketones, hydrocarbons, nitriles, esters other than the ester of our invention, lactones, natural essential oils and synthetic essential oils may be admixed so that the combined odors of the individual components produce a pleasant and desired fragrance, particularly and preferably in leather fragrances. Such perfume compositions usually contain (a) the main note or "bouquet" or foundation stone of the composition; (b) modifiers which round off and accompany the main note; (c) fixatives which include odorous substances which lend a particular note to the perfume throughout all stages evaporation and substances which retard evaporation; and (d) topnotes which are usually low boiling fresh smelling materials.

In perfume compositions, it is the individual components which contribute to their particular olfactory characteristics, however, the overal sensory effect of the perfume composition will be at least the sum total of the effects of each of the ingredients. Thus, the 4(2'-butyl) phenyl acetate of our invention having the structure:

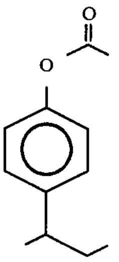

can be used to alter, modify or enhance the aroma characteristics of a leather perfume composition, for example, by utilizing or moderating the olfactory reaction contributed by another ingredient in the composition.

The amount of the 4(2'-butyl) phenyl acetate of our invention which will be effective in perfume compositions as well as perfumed articles, colognes and perfumed polymers depends on many factors including the other ingredients, their amounts and the effects which are desired. It has been found that perfume compositions containing as little a 0.01% of the 4(2'-butyl) phenyl acetate of our invention defined according to the structure:

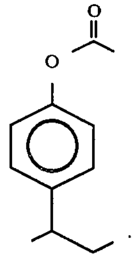

or even less (e.g., 0.005%) can be used to impart a leathery and ylang oil-like aroma with sweet and floral topnotes to soaps, anionic, cationic or nonionic detergents, fabric softener articles (such as BOUNCE®, a registered trademark of the Procter & Gamble Company of Cicinnati, Ohio), cosmetics or other products. The amount employed can range up to 70% of the fragrance components and will depend on considerations of cost, nature of the end product, the effect desired on the finished product and the particular fragrance sought.

The 4(2'-butyl) phenyl acetate of our invention is useful (taken alone or together with other ingredients in perfume compositions) as (an) olfactory component(s) in solid and liquid anionic, cationic and nonionic detergents and soaps, space odorants and deodorants, perfumes, colognes, toilet water, bath preparations such as creams, deodorants, hand lotions and sun screens; powders, such as talcs, dusting powders, face powders, perfumed polymers which include perfumed polyethylene and polypropylene and perfumed nylon. When used as an olfactory component, as little as 0.1% of the 4(2'-butyl) phenyl acetate of our invention will suffice to impart an intense long lasting leathery and ylang oil-like aroma with sweet and floral topnotes to "leather" perfume formulations. Generally, no more than 5% of the 4(2'-butyl) phenyl acetate of our invention based on the ultimate end product is required in the perfume composition.

In addition, the perfume compositions or fragrance compositions of our invention can contain a vehicle or carrier for the 4(2'-butyl) phenyl acetate of our invention. The vehicle can be a liquid such as an alcohol, e.g., ethanol, a non-toxic glycol such as propylene glycol or the like. The carrier can also be an absorbent solid such as gum (e.g., gum arabic, xanthan gum or guar gum) or components for encapsulating the composition (such as gelatin, for example, by means of coacervation or, for example, a urea-formaldehyde prepolymer when forming a urea-formaldehyde polymer capsule wall around a liquid fragrance center).

The range of use of the 4(2'-butyl) phenyl acetate of our invention in perfumed articles can vary from about 0.1% up to about 5% by weight of said perfumed article.

The following Example I serves to illustrate a process for preparing the 4(2'-butyl) phenyl acetate of our invention. The examples following Example I, e.g., Example II, et seq, serve to illustrate our invention. However, our invention is not intended to be limited thereto but is only intended to be limited insofar as the claims are concerned. All parts and percentages given herein are by weight unless otherwise specified.

EXAMPLE I

PREPARATION OF 4(2'-BUTYL) PHENYL ACETATE

Reaction:

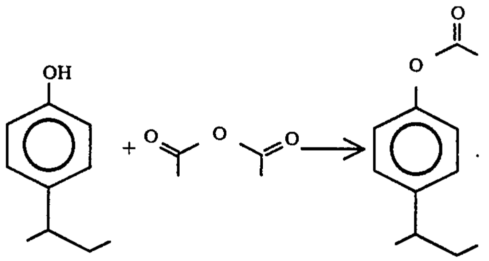

Into a 1 liter reaction flask equipped with stirrer, thermometer, reflux condenser, addition funnel and heating mantle is placed 150 grams of 4(2'-butyl) phenol in 200 ml toluene. The reaction mass with stirring is heated to reflux and while refluxing, dropwise over a period of one hour, 122 grams of acetic anhydride (1.2 moles) is added to the reaction mass. After the one hour period, the reaction mass is refluxed for an additional one hour. The reaction mass is then cooled to room temperature and 100 ml water is added. The resulting mixture is heated to 60° C. for one hour with stirring. The organic phase is separated from the aqueous phase and the organic phase is washed with concentrated salt solution followed by water followed by saturated sodium carbonate solution. The organic phase is then dried over anhydrous magnesium sulfate and distilled on a 12" Goodloe column yielding the following fractions:

| FRACTION NO. | VAPOR TEMP. (°C.) | LIQUID TEMP. (°C.) | VACUUM PSI (ABSOLUTE) |
|---|---|---|---|
| 1 | 24/24 | 65/110 | 2/2 |
| 2 | 72/74 | 85/86 | 2/2 |
| 3 | 79 | 92 | 1.0 |
| 4 | 79 | 93 | 0.8 |
| 5 | 78 | 92 | 2.0 |
| 6 | 78 | 92 | 1.0 |
| 7 | 78 | 91 | 1.0 |
| 8 | 78 | 92 | 1.0 |
| 9 | 78 | 92 | 1.0 |
| 10 | 75 | 95 | 1.0 |
| 11 | 60 | 144 | 0.6 |
| 12 | 63 | 186 | 0.6 |

Bulked fractions 3-9 have an excellent long lasting leathery and ylang aroma with sweet, floral topnotes. From a flavor standpoint, the resulting product has an interesting nutty aroma and taste profile causing it to be useful in creation of nut and vanilla flavors and in augmenting or enhancing the aroma or taste of nut or vanilla flavored foodstuffs at the level of from about 0.3 up to about 0.8 ppm.

EXAMPLE II

"LEATHER FRAGRANCE"

The following fragrance formulation is prepared:

| INGREDIENTS | WEIGHT PERCENT |
|---|---|
| The 4(2'-butyl) phenyl having the structure: 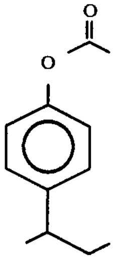 | 4% |
| Methyl decyl ketone | 5% |
| 1,3,5-trimethyl-4-ethyl benzene | 5% |
| 2,4-di-isopropyl phenol | 5% |
| Ethyl laurate | 40% |
| n-Decane | 41% |

The foregoing formulation is compared to a formulation identical except without the 4(2'-butyl) phenyl acetate having the structure:

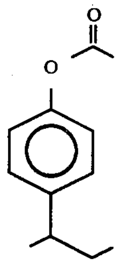

A bench panel of five members unanimously agrees that the formulation without the compound having the structure:

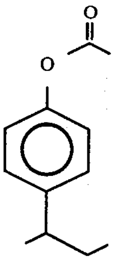

lacks the intense natural-like ylang, floral notes so important to creation of a natural leather fragrance.

The above perfume formulation is described as "leathery with an ylang oil-like undertone and sweet, floral topnotes".

EXAMPLE III

PREPARATION OF COSMETIC POWDER COMPOSITION

Cosmetic powder compositions are prepared by mixing in a ball mill 100 grams of talcum powder (per composition) with 0.25 grams of each of the substances set forth in Table I below (per composition). Each of the cosmetic powder compositions has an excellent aroma as described in Table I below:

TABLE I

| SUBSTANCE | AROMA DESCRIPTION |
|---|---|
| The 4(2'-butyl) phenyl acetate having the structure: 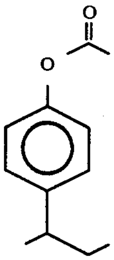 | A leathery and ylang oil-like aroma with sweet and floral topnotes |
| Perfume composition of Example II | A leathery aroma with an ylang oil-like undertone and sweet, floral topnotes. |

EXAMPLE IV

PERFUMED LIQUID DETERGENTS

Concentrated liquid detergents (lysine salt of n-dodecylbenzene sulfonic acid as more specifically described in U.S. Pat. No. 3,948,818, issued on Apr. 6, 1976 incorporated by reference with aroma nuances as set forth in Table I of Example III, are prepared containing 0.10%, 0.15%, 0.20%, 0.25%, 0.30% and 0.35% of the substance set forth in Table I of Example III. They are prepared by adding and homogeneously mixing the appropriate quantity of substance set forth in Table I of Example III in the liquid detergent. The detergents all possess excellent aromas as set forth in Table I of Example III, the intensity increasing with greater concentrations of substance as set forth in Table I of Example III.

EXAMPLE V

PREPARATION OF COLOGNES AND HANDKERCHIEF PERFUMES

Compositions as set forth in Table I of Example III are incorporated into colognes at concentrations of 2.0%, 2.5% 3.0%, 3.5%, 4.0%, 4.5% and 5.0% in 80%, 85%, 90% and 95% aqueous food grade ethanol solutions; and into handkerchief perfumes at concentrations of 15%, 20%, 25% and 30% (in 80%, 85%, 90% and 95% aqueous food grade ethanol solutions). Distinctive and definitive fragrances as set forth in Table I of Example III are imparted to the colognes and to the handkerchief perfumes at all levels indicated.

EXAMPLE VI

PREPARATION OF SOAP COMPOSITIONS

One hundred grams of soap chips (per sample) (IVORY ® produced by the Procter & Gamble Company of Cincinnati, Ohio), are each mixed with one gram samples of substances as set forth in Table I of Example III until homogeneous compositions are obtained. In each of the cases, the homogeneous compositions are heated under 8 atmospheres pressure at 180° C. for a period of three hours and the resulting liquids are placed into soap molds. The resulting soap cakes, on cooling, manifest aromas as set forth in Table I of Example III.

EXAMPLE VII

PREPARATION OF SOLID DETERGENT COMPOSITIONS

Detergents are prepared using the following ingredients according to Example I of Canadian Pat. No. 1,007,948 (incorporated by reference herein):

| INGREDIENT | PERCENT BY WEIGHT |
|---|---|
| Neodol ® 45-11 (a $C_{14}$-$C_{15}$ alcohol ethoxylated with 11 moles of ethylene oxide) | 12 |
| Sodium carbonate | 55 |
| Sodium citrate | 20 |
| Sodium sulfate, water brightners | q.s. |

This detergent is a phosphate-free detergent. Samples of -100 grams each of this detergent are admixed with 0.10, 0.15, 0.20 and 0.25 grams of each of the substances as set forth in Table I of Example III. Each of the detergent samples has an excellent aroma as indicated in Table I of Example III.

EXAMPLE VIII

Utilizing the procedure of Example I at column 15 of U.S. Pat. No. 3,632,396 (the disclosure of which is incorporated by reference), nonwoven cloth substrates useful as dryer-added fabric softening articles of manufacture are prepared wherein the substrate, the substrate coating, the outer coating and the perfuming material are as follows:

1. A water "dissolvable" paper ("Dissolvo Paper");
2. Adogen 448 (m.p. about 140° F.) as the substrate coating; and
3. An outer coating having the following formulation (m.p. about 150° F.):
   57% $C_{20-22}$ HAPS
   22% isopropyl alcohol
   20% antistatic agent
   1% of one of the substances as set forth in Table I of Example III.

Fabric softening compositions prepared according to Example I at column 15 of U.S. Pat. No. 3,632,396 having aroma characteristics as set forth in Table I of Example III, supra, consist of a substrate coating having a weight of about 3 grams per 100 square inches of substrate; a first coating located directly on the substrate coating consisting of about 1.85 grams per 100 square inches of substrate; and an outer coating coated on the first coating consisting of about 1.4 grams per 100 square inches of substrate. One of the substances of Table I of Example III is admixed in each case with the outer coating mixture, thereby providing a total aromatized outer coating weight ratio to substrate of about 0.51:1 by weight of the substrate. The aroma characteristics are imparted in a pleasant manner to the head space in a dryer on operation thereof in each case using said dryer-added fabric softener nonwoven fabrics and these aroma characteristics are described in Table I of Example III, supra.

EXAMPLE IX

HAIR SPRAY FORMULATIONS

The following hair spray formulation is prepared by first dissolving PVP/VA E-735 copolymer manufactured by the GAF Corporation of 140 West 51st Street, New York, N.Y. in 91.62 grams of 95% food grade ethanol. 8.0 Grams of the polymer is dissolved in the alcohol. The following ingredients are added to the PVP/VA alcoholic solution:

| INGREDIENTS | PERCENT BY WEIGHT |
|---|---|
| Dioctyl sebacate | 0.05% |
| Benzyl alcohol | 0.10% |
| Dow Corning 473 fluid (prepared by the Dow Corning Corporation) | 0.10% |
| Tween 20 surfactant (prepared by ICI America Corporation) | 0.03% |
| One of the perfumery substances as set forth in Table I of Example III, supra | 0.10% |

The perfuming substances as set forth in Table I of Example III add aroma characteristics as set forth in Table I of Example III which are rather intense and aesthetically pleasing to the users of the soft-feel, good-hold pump hair sprays.

EXAMPLE X

CONDITIONING SHAMPOOS

Monamid CMA (prepared by the Mona Industries Company) (3.0 weight percent) is melted with 2.0 weight percent coconut fatty acid (prepared by Procter & Gamble Company of Cincinnati, Ohio); 1.0 weight percent ethylene glycol distearate (prepared by the Armak Corporation) and triethanolamine (a product of Union Carbide Corporation) (1.4 weight percent). The resulting melt is admixed with Stepanol WAT produced by the Stepan Chemical Company (35.0 weight percent). The resulting mixture is heated to 60° C. and mixed until a clear solution is obtained (at 60° C.). This material is "Composition A".

Gafquat® 755 N polymer (manufactured by GAF Corporation of 140 West 51st Street, New York, N.Y.) (5.0 weight percent) is admixed with 0.1 weight percent sodium sulfite and 1.4 weight percent polyethylene glycol 6000 distearate produced by Armak Corporation. This material is "Composition B".

The resulting Composition A and Composition B are then mixed in a 50:50 weight ratio of A:B and cooled to 45° C. and 0.3 weight percent of perfuming substance as set forth in Table I of Example III is added to the mixture. The resulting mixture is cooled to 40° C. and blending is carried out for an additional one hour in each case. At the end of this blending period, the resulting material has a pleasant fragrance as indicated in Table I of Example III.

EXAMPLE XI

PERFUMED POLYMER

Scented polyethylene pellets having a pronounced leather aroma are prepared as follows:

75 Pounds of polyethylene of a melting point of about 220° F. were heated to about 230° F. in a container of the kind illustrated in FIGS. 1 and 2 of U.S. Pat. No. 3,505,432, the disclosure of which is incorporated by reference herein. 25 Pounds of the leather aroma formulation of Example II were then quickly added to the liquified polyethylene, the lid was put in place and the agitating means were actuated. The temperature was maintained at about 225° F. and the mixing was continued for about 5-15 minutes. The valve was then opened to allow flow of the molten polyethylene enriched with the leather aroma-containing material to exit through the orifices. The liquid falling through the orifices solidified almost instantaneously upon impact with the moving cooled conveyor. Solid polyethylene beads or pellets having a pronounced leather aroma scent were thus formed (green, violet, floral, woody, peppery and amber undertones). Analysis demonstrated that the pellets contained about 25% of the leather aroma formulation of Example II so that almost no losses of the scenting substance did occur. These pellets may be called master pellets. .'

50 Pounds of the leather aroma containing master pellets were then added to 1000 pounds of unscented polyethylene powder and the mass was heated to the liquid state in the equipment of U.S. Pat. No. 3,505,432. The liquid was molded into thin sheets of films. The thin sheets or films had a pronounced leather aroma and were used in standard air freshening/scenting equipment.

EXAMPLE XII

A. AUGMENTING AND ENHANCING THE AROMA AND TASTE OF A VANILLA CARBONATED BEVERAGE

To a flavor oil containing 95% natural vanilla and 5% natural lemon oil is added at the rate of 0.4 ppm, the compound having the structure:

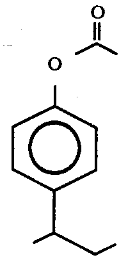

prepared according to Example I. The resulting oil is made up into a carbonated beverage entitled "cream soda" according to standard carbonation techniques. The resulting "cream soda" has a more natural aesthetically pleasing taste and is unanimously preferred by a bench panel over the same "cream soda" without the compound having the structure:

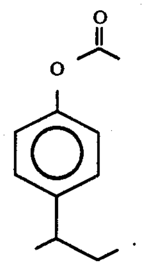

B. PREPARATION OF PUREE CHESTNUT DESSERT

At the rate of 4 ppm the compound having the structure:

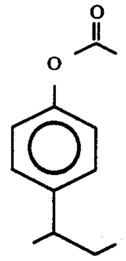

is added to a standard Hungarian puree chestnut dessert. The compound having the structure:

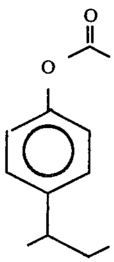

imparts aesthetically pleasing natural-like aroma and taste nuance to this chestnut dessert making it taste more natural-like after four weeks storage in a refrigerator. A bench panel of five members unanimously prefers the chestnut dessert containing the compound having the structure:

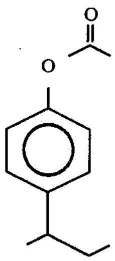

over the chestnut dessert not containing this compound after three weeks storage in the refrigerator.

What is claimed is:

1. A process for augmenting, enhancing or imparting a leathery aroma in or to perfume compositions, colognes, perfumed polymers or perfumed articles comprising the step of adding to a perfume composition, a cologne, a polymer or an article capable of being perfumed a leather aroma augmenting, enhancing or imparting quantity of the 4(2'-butyl) phenyl acetate having the structure:

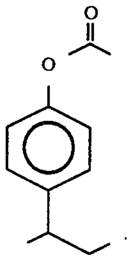

2. The process of claim 1 wherein the 4-(2'-butyl) phenyl acetate having the structure:

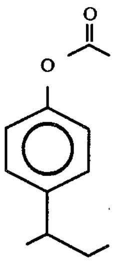

is added to a perfume composition.

3. The process of claim 1 wherein the 4(2'-butyl) phenyl acetate having the structure:

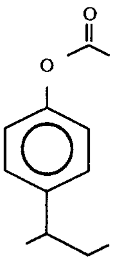

is added to a polymer.

4. The process of claim 1 wherein the 4(2'-butyl) phenyl acetate having the structure:

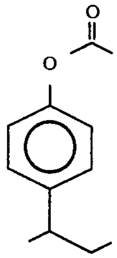

is added to a cologne.

5. The process of claim 1 wherein the 4(2'-butyl) phenyl acetate having the structure:

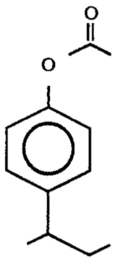

is added to an article capable of being perfumed and the article is a solid or liquid anionic, cationic, nonionic or zwitterionic detergent.

6. The process of claim 1 wherein the 4(2'-butyl) phenyl acetate having the structure:

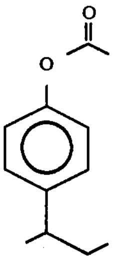

is added to an article capable of being perfumed selected from the group consisting of fabric softener compositions and fabric softener articles.

7. A process for augmenting or enhancing the aroma of a nut or a vanilla-flavored foodstuff comprising the step of adding to said foodstuff an aroma or taste augmenting quantity of the compound having the structure:
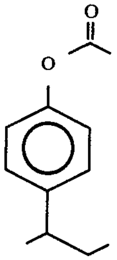
8. The process of claim 7 wherein the compound having the structure:
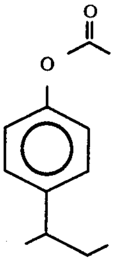
is added to a vanilla flavored carbonated beverage.
* * * * *